United States Patent
Dellaca' et al.

(10) Patent No.: US 8,689,787 B2
(45) Date of Patent: Apr. 8, 2014

(54) APPARATUS FOR RESPIRATORY SUPPORT AND NON-INVASIVE DETECTION OF ALVEOLAR DERECRUITMENT FOR PATIENTS SUFFERING FROM RESPIRATORY FAILURE

(75) Inventors: Raffaele Dellaca', Como (IT); Andrea Aliverti, Como (IT); Antonio Pedotti, Como (IT)

(73) Assignee: Politecnico di Milano, Milan (IT)

( * ) Notice: Subject to any disclaimer, the term of this patent is extended or adjusted under 35 U.S.C. 154(b) by 664 days.

(21) Appl. No.: 12/441,183

(22) PCT Filed: Sep. 11, 2007

(86) PCT No.: PCT/EP2007/059534
§ 371 (c)(1),
(2), (4) Date: Mar. 13, 2009

(87) PCT Pub. No.: WO2008/031822
PCT Pub. Date: Mar. 20, 2008

(65) Prior Publication Data
US 2009/0272381 A1 Nov. 5, 2009

(30) Foreign Application Priority Data
Sep. 14, 2006 (IT) ................................. MI06A1755

(51) Int. Cl.
*A61M 16/00* (2006.01)
*A62B 7/00* (2006.01)
*F16K 31/02* (2006.01)

(52) U.S. Cl.
USPC ............. 128/204.23; 128/204.18; 128/204.21

(58) Field of Classification Search
USPC ............. 128/200.24, 200.26, 204.18, 204.19, 128/204.21–204.24, 897, 898; 600/532, 600/533
See application file for complete search history.

(56) References Cited

U.S. PATENT DOCUMENTS 4,972,842 A * 11/1990 Korten et al. .................. 600/529
5,318,038 A * 6/1994 Jackson et al. ................ 600/533

(Continued)

FOREIGN PATENT DOCUMENTS

EP        1 551 293       7/2005
WO        03/103493       12/2003

OTHER PUBLICATIONS

R.L. Dellaca et. al., Detection of expiratory flow limitation in COPD using the forced oscillation technique, European Respiratory Journal 2004, pp. 232-240 (9 pages total).*

(Continued)

*Primary Examiner* — Oren Ginsberg
(74) *Attorney, Agent, or Firm* — Ladas & Parry LLP (57) ABSTRACT

There is described an apparatus (1) for respiratory support and non-invasive detection of alveolar derecruitment for patients suffering from respiratory failure. Such an apparatus (1) generally comprises a mechanical ventilator (3) for inspiration/expiration functions and means (15) allowing to impose an additional periodic pressure component (Pstim) having a higher frequency than the spectral content of the inspiration/expiration pressure component (Presp). There are provided computing means (12) to obtain the inspiratory average reactance (Xrs) of the respiratory system of the patient (2) as the positive end-expiratory pressure (PEEP) varies, in order to detect the presence of alveolar derecruitment. There is also described a procedure allowing to obtain an optimal positive end-expiratory pressure.

8 Claims, 6 Drawing Sheets

(56) References Cited

U.S. PATENT DOCUMENTS

| | | | |
|---|---|---|---|
| 5,513,648 A * | 5/1996 | Jackson | 600/529 |
| 6,142,952 A | 11/2000 | Behbehani et al. | |
| 6,435,182 B1 * | 8/2002 | Lutchen et al. | 128/204.21 |
| 7,122,010 B2 * | 10/2006 | Bohm et al. | 600/536 |
| 7,325,545 B2 * | 2/2008 | Dellaca' et al. | 128/204.23 |
| 2008/0114261 A1 * | 5/2008 | Dellaca et al. | 600/529 |
| 2010/0147305 A1 * | 6/2010 | Dellaca' et al. | 128/204.23 |
| 2010/0275921 A1 * | 11/2010 | Schindhelm et al. | 128/204.23 |

OTHER PUBLICATIONS

Ferre, R., et al. "Servocontrolled generator to measure respiratory impedance from 0.25 to 26 Hz in ventilated patients at different PEEP levels." *European Respiratory Journal* (1995) vol. 8, No. 7 pp. 1222-1227.

Peslin, R., et al. "Respiratory mechanics studied by forced oscillations during artificial ventilation." *European Respiratory Journal* ((1993) vol. 6, No. 6 pp. 772-784.

Fu-Chung, Y., et al. "A Nonnvasive Technique for Detecting Obstructive and Central Sleep Apnea." *IEEE Transactions on Biomedical Engineering* (1997) vol. 44, No. 12 pp. 1262-1268.

* cited by examiner

APPARATUS FOR RESPIRATORY SUPPORT AND NON-INVASIVE DETECTION OF ALVEOLAR DERECRUITMENT FOR PATIENTS SUFFERING FROM RESPIRATORY FAILURE

The present invention relates to an apparatus for respiratory support and non-invasive detection of alveolar derecruitment for patients suffering from respiratory failure.

The phenomenon of the so-called "alveolar derecruitment" (hereafter also referred to as "derecruitment"), due to diseases of the respiratory system causing respiratory failure and to pharmacologically induced anaesthesias or paralyses, is known.

Alveolar derecruitment consists in the alveolar spaces collapsing as a consequence of the reduction of the concentration of surfactant or the obstruction of the peripheral airways. Such phenomena are due to the build-up of edema because of the action of inflammatory processes and to the use of oxygen concentrations in the inhaled gas higher than those of the air in the environment, which is associated to low pulmonary volumes due to a supine position and to the use of anaesthetics.

The parts of lung which are affected by derecruitment do not take part in pulmonary gaseous exchanges, thus causing the reduction of the oxygenation of the blood and the death of the patient.

In order to counteract this phenomenon, a ventilatory support is applied in the clinical practice, for instance a mechanical ventilator, which ensures a so-called "Positive End-Expiratory Pressure" (also known by the acronym PEEP), with the aim of opening up again the regions affected by derecruitment and holding them open and ventilated (it must be noted that hereafter the pressure is considered in relation to the atmospheric pressure and is expressed in cmH$_2$O units; "zero pressure" means "atmospheric pressure" and is equivalent to 0 cmH$_2$O; "positive pressure" means "pressure higher than atmospheric pressure").

This operation of imposing a positive end-expiratory pressure is designated "alveolar recruitment" (or more simply "recruitment").

Figure 4:
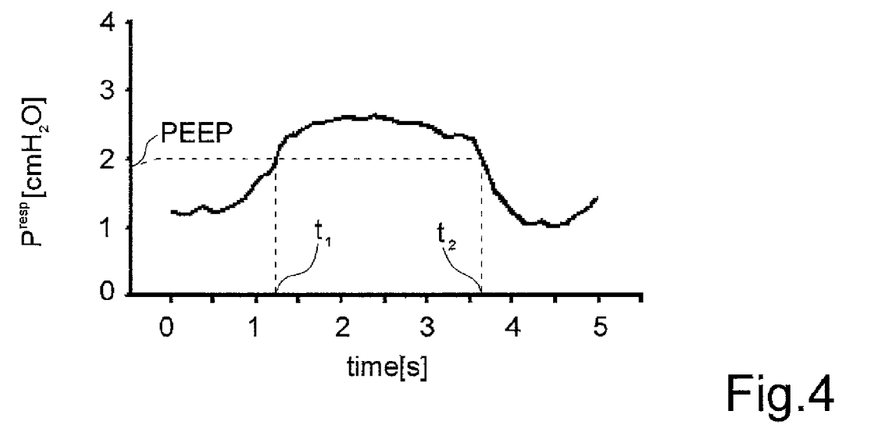
FIG. 4 shows the trend of the respiratory pressure component ($P^{resp}$) due to a mechanical ventilator in the course of time.
Figure 9:
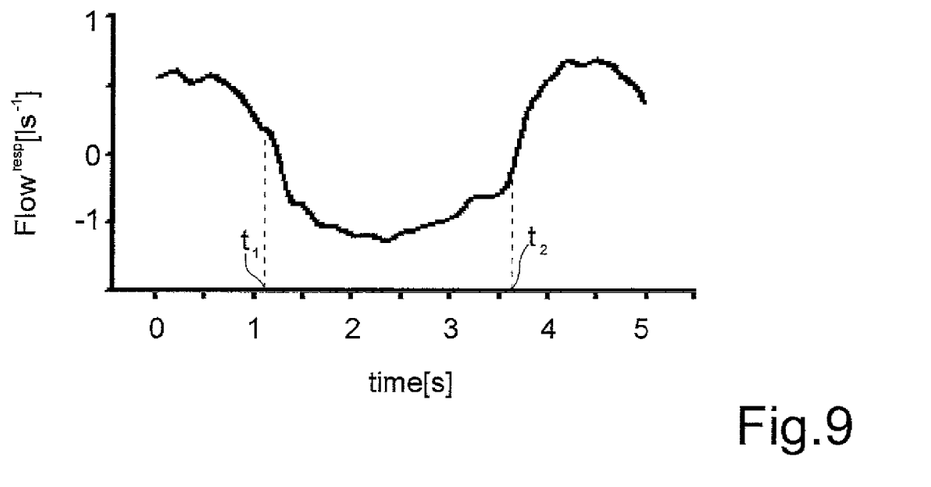
FIG. 9 shows the trend of a low frequency flow component (Flow$^{resp}$) in the course of time.

FIG. 4 shows the trend of the respiratory pressure $P^{resp}$ of a patient subjected to ventilation with positive end-expiratory pressure in the course of time; the trend of the air flow (Flow$^{resp}$) related to the same breath is shown in FIG. 9. Conventionally, the inflow into the patient is considered positive (that is, during inspiration). The measurement unit of such a flow is hereinafter litres per time unit (l/s).

The patient inhales (Flow$^{resp}$>0) in the range of time between 0 and $t_1$; the patient exhales (Flow$^{resp}$<0) in the range of time between $t_1$ and $t_2$, and then inhales again after time $t_2$.

It must be noted that at time $t_2$, at the end of the expiration, the pressure is positive and equivalent to the PEEP ($P^{resp}$=PEEP>0). Without the mechanical ventilator, the respiratory pressure would be near zero, and $P^{resp}$ would be negative during the inspiratory phase.

The positive end-expiratory pressure value should carefully be determined, as too low a pressure does not allow to open up the lung again, whereas too high a pressure causes further damage to the parenchyma enhancing the inflammatory condition and often has very dangerous consequences for the patient. Such consequences are known by the term "VILI", which is the acronym of the term "Ventilator-Induced Lung Injury".

Currently, there are no non-invasive and automatic apparatuses to quantify the presence of derecruitment and estimate how the latter may vary as the positive end-expiratory pressure varies, therefore the setting of this important parameter is left to the experience and to the insight of the clinician, with the result that the positive end-expiratory pressure values are sometimes not optimal.

The best available procedure for the identification of the optimal positive end-expiratory pressure consists in carrying out a static pressure-volume curve obtained by the known super-syringe method which, however, may not be employed in the clinical practice as it implies that the patient is sedated, paralysed and that he/she does not breathe for long periods.

The article "Respiratory mechanics studied by forced oscillations during artificial ventilation" di Peslin R. et al, European respiratory journal, MUNKSGAARD INTERNATIONAL PUBLISHER, Copenaghen, DK, vol. 6, no. 6, 1993, pages 772-784, the article "A non invasive tecnique for detecting obstructive and central sleep apnea" di Fu-chung Yen et al., IEEE TRANSACTION OF BIOMEDICAL ENGINEERING, IEEE service center, Piscataway, N.J., US, vol. 44, no. 12, Dec. 1997, the article "Servocontrolled generator to measure respiratory impedance from 0.25 to 26 hz in ventilated patients at different peep levels" di Farre R et al, European respiratory journal, MUNKSGAARD INTERNATIONAL PUBLISHER, Copenaghen, DK, vol. 8, no. 7, Jul. 1995, pages 1222-1227 and U.S. Pat. No. 6,142,952 discloses an apparatus for respiratory support and non-invasive detection of alveolar derecruitment for patients suffering from respiratory failure as defined in the preamble of claim 1.

It is the object of the present invention to obtain a non-invasive system for the detection of the variations of alveolar recruitment, so as to obtain the optimal positive end-expiratory pressure without interrupting ventilation.

According to the invention, such an object is achieved by means of an apparatus for respiratory support and non-invasive detection of alveolar derecruitment for patients suffering from respiratory failure as defined in claim 1.

Said means allowing to carry out the respiratory functions are generally means adapted to carry out the inspiratory and expiratory operations with the possibility of imposing a positive end-expiratory pressure; they usually comprise a mechanical ventilator. The mechanical ventilator itself may also be able to generate said additional pressure.

The inspiratory reactance is generally obtained as the average of the instantaneous reactance value over the inspiratory step of a breath or part of it, but it could also be an indicative value, for instance the median value over a breath, the maximum value, or the average value related to half a breath or even another value.

In some embodiments, the computing means automatically control the mechanical ventilator and may thus set the positive end-expiratory pressure according to algorithms adapted to determine, at least approximately, the maximum value of inspiratory reactance (described hereafter) and the positive end-expiratory pressure associated thereto, which is the optimal positive end-expiratory pressure.

The additional pressure component is generally overlapped to the pressure imposed by the mechanical ventilator by the action of external devices, such as speakers or modulating valves (such as voice-coil actuators) or due to the mechanical ventilator itself.

The additional pressure component may also be obtained as the harmonic of an impulse or pressure. In this case, filters need to be used allowing to cut the frequencies which are too low or too high.

However, as a variant, systems based on the known art, such as HFOV based on the use of high frequency mechanical ventilators, may also be used. Such a technique consists in delivering tidal volumes by means of the application of high frequency oscillatory pressures overlapped to a continuous distension pressure at the entrance of the airways. Such a technique is described in the paper: "High-frequency oscillatory ventilation: Mechanisms of gas exchange and lung mechanics", J. Jane Pillow, Crit. Care Med. 2005, vol. 33, issue 3 (suppl.). By means of such a technique the main ventilation parameter is the continuous distension pressure, generally known by the acronym CDP. From an operative point of view, the continuous distension pressure has the same role as the positive end-expiratory pressure. In such systems, the frequency of the respiratory pressure is suitable to detect the inspiratory reactance even without the need of further means.

The invention also relates to an automatic or manual procedure for the non-invasive monitoring of the variations of the alveolar recruitment of a patient with respiratory failure.

By means of such a procedure, an additional pressure component oscillating at frequencies higher than the spectral content of the breath is overlapped to the normal respiratory pressure having a periodic trend imposed by a mechanical ventilator.

Figure 5:
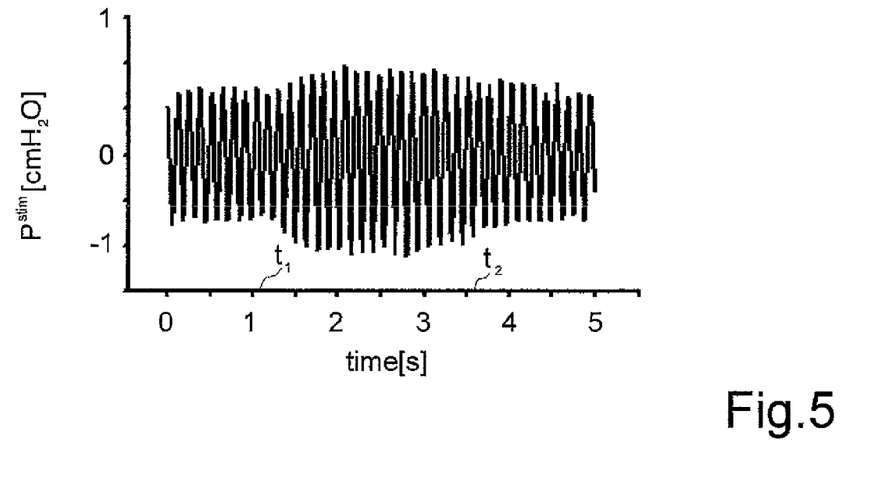
FIG. 5 shows the trend of the additional pressure component ($P^{stim}$) in the course of time.

An example of additional pressure component, designated by $P^{stim}$, is shown in FIG. 5. $P^{stim}$ is added up to a respiratory pressure component imposed by the mechanical ventilator. Such a component is completely equivalent to the previously described $P^{resp}$ (the symbol of which will therefore be used) and is thus shown in FIG. 4. The same considerations concerning PEEP, $t_1$ e $t_2$ apply thereto.

Figure 6:
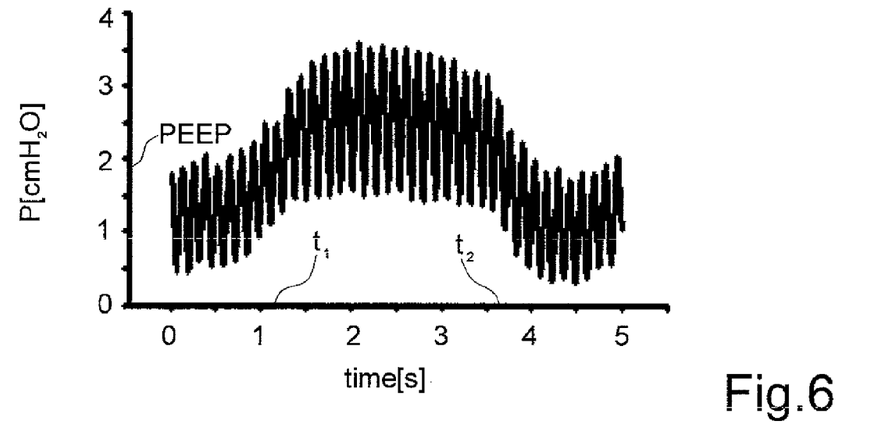
FIG. 6 shows the trend of the pressure ($P=P^{resp}+P^{stim}$) to which the respiratory system of a patient is subjected by means of a device according to the invention in the course of time.

The total pressure, to which the respiratory system of a patient is subjected, designated by P and shown in FIG. 6, is therefore obtained from the sum of $P^{stim}$ (FIG. 5) and $P^{resp}$ (FIG. 4).

Figure 7:
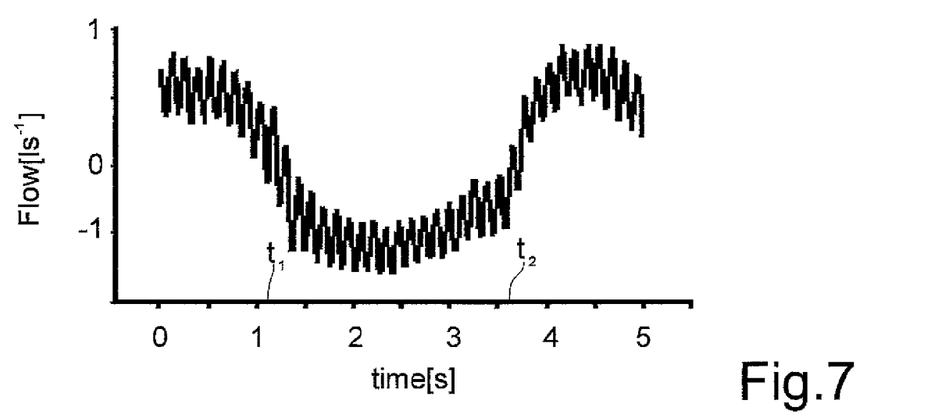
FIG. 7 shows the trend of the air flow (Flow) to which the respiratory system of a patient is subjected by means of a device according to the invention in the course of time.
Figure 8:
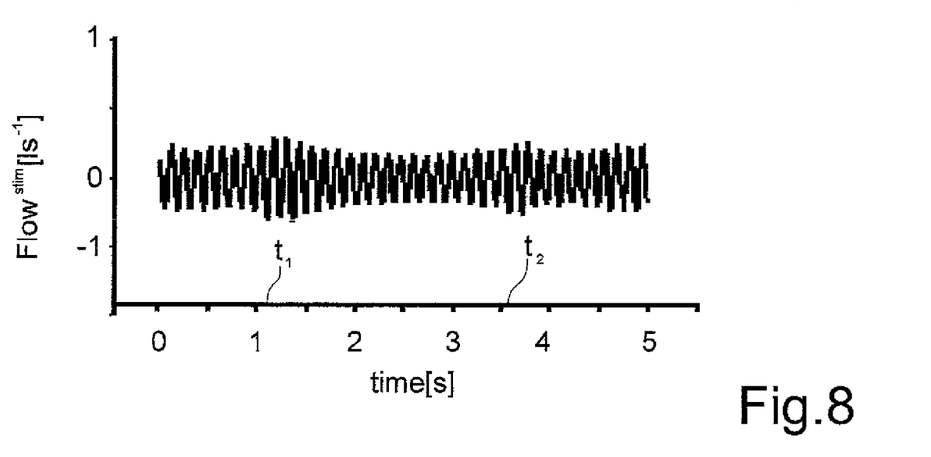
FIG. 8 shows the trend of a high frequency flow component (Flow$^{stim}$) in the course of time.

The high frequency flow component $Flow^{stim}$ (FIG. 8), the low frequency flow component $Flow^{resp}$ (FIG. 9) and the total flow, which is the sum of such components, Flow (FIG. 7) respectively correspond to $P^{stim}$, $P^{resp}$ and P.

It is known that an equivalence may be made between a respiratory system and an electric system, and that by the measurement of flows and pressures of the respiratory system (converted to currents and voltages in the equivalent electrical system) the trend of the input impedance of the total intra-breath respiratory system may be computed, for instance as described by Dellacà, Santus, Aliverti, Stevenson, Centanni, Macklem, Pedotti e Calverley in "*Detection of expiratory flow limitation in COPD using the forced oscillation technique*", Eur. Respir. J 23:232-240, year 2004.

To obtain the optimal positive end-expiratory pressure, the respiratory system of a patient is initially subjected to an end-expiratory pressure which is certainly lower than the optimal positive end-expiratory pressure of the patient (for instance at a zero pressure). Then, the value of the positive end-expiratory pressure is modified, at first obtaining a progressive increase (insufflating step) followed by a progressive decrease (desufflating step) down to zero $cmH_2O$ or to a predetermined minimum value. During this procedure and for every value of the positive end-expiratory pressure, the inspiratory is evaluated, which is the average value of the imaginary part taken by the impedance during the inspiratory step, as described in the previously mentioned scientific paper and also by Dellacà, Rotger, Aliverti, Navajas, Pedotti e Farrè in "*Non-invasive detection of expiratory flow limitation in COPD patients during nasal CPAP*", in *Eur.Respir.J*, year 2006. It must be noted that the inspiratory reactance of patient 2 (that is, not during expiration) must be considered, so that no distortive effects, due to the possible presence of limitations in the expiratory flow, are obtained. The inspiratory reactance is designated by $X_{rs}$; it is expressed in $$cmH_2O\frac{s}{l},$$

where s are seconds and l are liters of air. A computing method to obtain the inspiratory reactance value $X_{rs}$ will be described at the end of this description.

Figure 2:
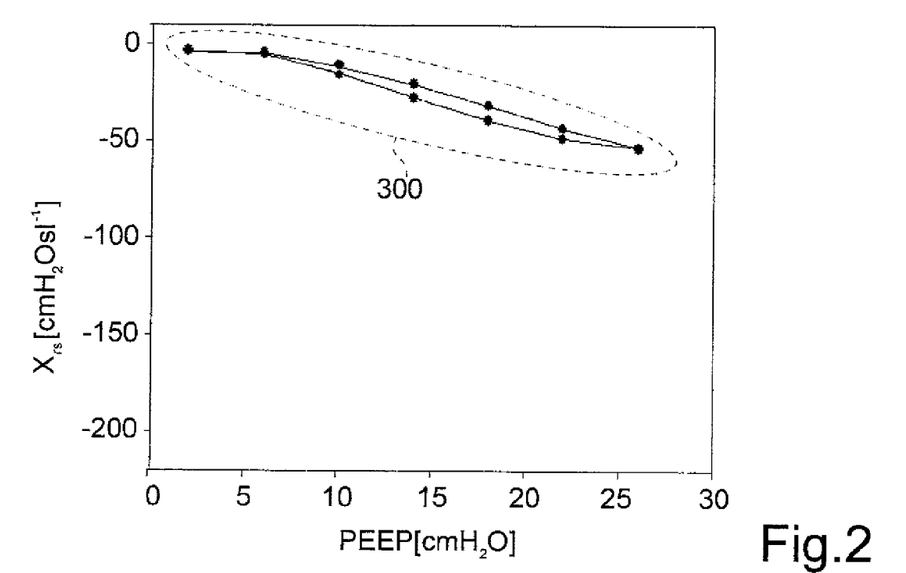
FIG. 2 shows the trend of the inspiratory average reactance ($X_{rs}$) as a function of the positive end-expiratory pressure (PEEP) in a patient without recruitment.
Figure 3:
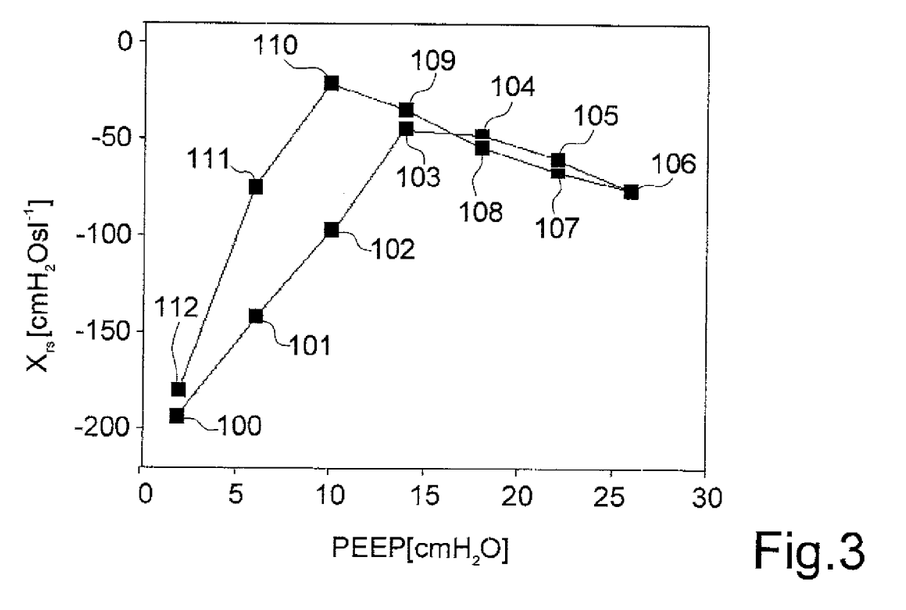
FIG. 3 shows the trend of the inspiratory average reactance ($X_{rs}$) as a function of the positive end-expiratory pressure (PEEP) in a patient with recruitment.

A graph of the resulting values is plotted at the end of the measurements obtained in the insufflating and desufflating step. FIG. 2 shows the graph 300 of a patient having no derecruitment. FIG. 3 shows the graph of a patient having derecruitment. The detection of the phenomenon of derecruitment may therefore be observed with the naked eye. In FIG. 3 the samples obtained during the insufflating step (from 100 to 106) and those obtained during the desufflating step (106 a 112) may be noted.

The graph of FIG. 3 is characterised by a marked hysteresis. The value of the inspiratory reactance obtained at lower values of positive end-expiratory pressure results being lower if the portion of lung affected by derecruitment is broader.

When the positive end-expiratory pressure (from 100 to 103) increases, in case of recruitment of new alveolar units, the inspiratory reactance progressively increases.

At a certain point, the increase of the working pressures leads to an overdistension of the lung thus causing a reduction in compliance and, therefore, the inspiratory average reactance starts to decrease again (from 104 to 106), thus reversing the trend as a function of the positive end-expiratory pressure.

Similarly, during the desufflating step (from 106 to 112), an increase of the inspiratory reactance occurs at first (from 106 to 110), due to the elimination of the overdistension, followed by a decrease (from 106 to 112) due to the collapse of alveolar units and to the lung closing up again.

The maximum of the desufflating curve (110) represents the best compromise between the recruitment of new alveolar units and the overdistension of the already open parts. The difference between the inspiratory curve (from 100 to 106) and the expiratory curve (from 106 to 112) is due to the effect of the hysteresis associated to the recruitment: once the lung is opened up again, lower pressures are sufficient to obtain a given degree of pulmonary recruitment with respect to those required for the opening.

The value of the inspiratory reactance may be monitored breath by breath to detect derecruitment phenomena in the course of time and identify the best moment for a new recruitment manoeuvre.

Therefore, once the maximum of the desufflating curve (110) is known, ventilation with the positive end-expiratory pressure corresponding to such a maximum point (110) may be performed.

These and other features of the present invention will become more apparent from the following detailed description of an embodiment thereof, shown by no limitation in the accompanying drawings, in which

Figure 1:
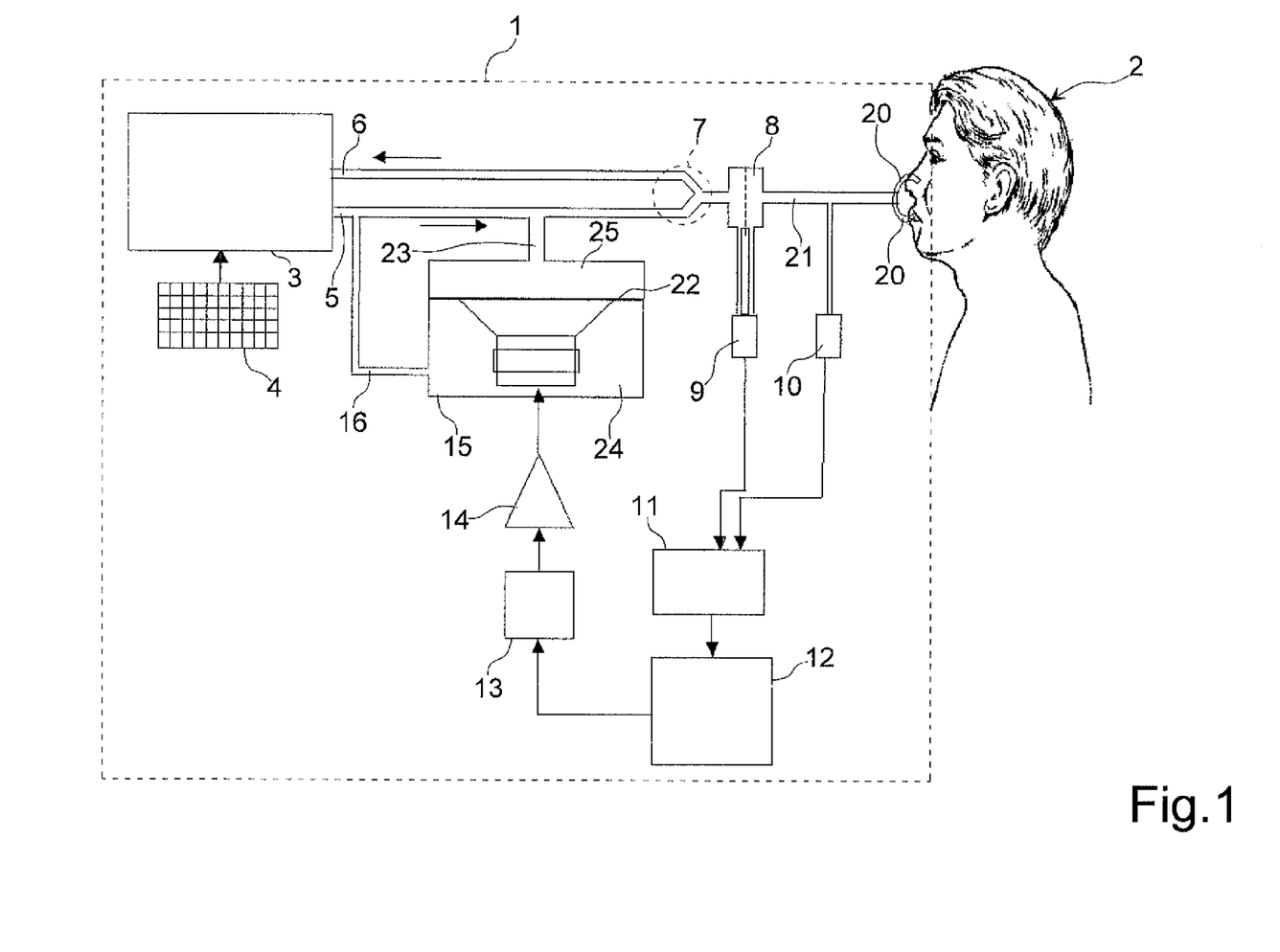
FIG. 1 shows a diagram of an apparatus according to the invention.

FIG. 1 shows an apparatus 1 according to the invention, applied to a patient 2.

In this embodiment, a mechanical ventilator 3 is provided for inspiration and expiration; it also allows to impose a positive end-expiratory pressure that may be set by a human operator by means of a keyboard 4.

The mechanical ventilator 3 is connected to an inspiration tube 5, in which it pumps air directed to the pulmonary system of the patient 2, and to an expiration tube 6, by means of which the mechanical ventilator 3 allows the passive expiration of the patient and the application of a positive end-expiratory pressure. The tubes 5 and 6 are connected in the pipe fitting 7. Connectors 20 connect the apparatus 1 to the airways of the patient 2.

Downstream of the pipe fitting 7, there is a traditional pneumotachograph 8 (for instance provided with Lilly, Silverman or Fleisch resistors), allowing to convert an air flow to a pressure difference; such a pneumotachograph 8 is connected to a transducer 9 that converts such a pressure value to an electric voltage. The cascade functioning of the devices 8 and 9 thus allows to obtain a voltage proportional to the respiratory flow of the patient.

Downstream of the pneumotachograph 8 there is a traditional pressure transducer 10 that converts the pressure P to an electric voltage.

The transducers 9 and 10 are both connected to an analogue-digital convertor 11 having two inputs: in the first input there is a value proportional to the flow, in the second input there is a value proportional to the pressure. Such an analogue-digital convertor 11 provides pressure and flow values in a digital format to an electronic processor 12, which, for every sampling carried out, computes the inspiratory average reactance and makes it available to the operator. On the basis of the data obtained, the operator modifies the positive end-expiratory pressure by means of the keyboard 4 associated to the mechanical ventilator.

The electronic processor 12 controls a speaker 15 as follows. The electronic processor 12 is connected in output to a digital-analogue convertor 13; the digital-analogue convertor 13 produces in output a voltage equivalent to the digital value obtained from the electronic processor 12.

Downstream of the digital-analogue convertor 13 there is a power amplifier 14, connected to the input of a speaker 15.

Such a speaker 15 comprises a membrane 22 that may shift (in a vertical direction with respect to FIG. 1) so as to increase or decrease the volume of the two chambers 24 and 25, separated by a membrane 22. Such a speaker 15 imposes, downstream of membrane 22 (chamber 25), a pressure component proportional to the output of the electronic processor 12.

The speaker 15 is connected to an inspiration tube 5 by means of the opening 23. In virtue of this connection, the pressure of the air inhaled by the patient 2 is subjected to an additional pressure component controlled by the electronic processor 12.

A long and narrow tube 16 is placed between the inspiration tube 5 and the chamber 24 of the speaker 15, the tube serving as a low pass filter to prevent the staving in of the membrane 22 due to excessive stresses between the chamber 25 and the chamber 24. The use of such a tube 16 is encompassed by the known technique.

Therefore, the respiration of the patient is subjected to a respiratory pressure due to two components:
a respiratory component P$^{resp}$ due to the mechanical ventilator 3;
an additional component P$^{stim}$ due to the speaker 15 controlled by the electronic processor 12.

The electronic processor 12 controls the speaker 15 so that this imposes the frequency of sinusoidal additional pressure component P$^{stim}$ at 5 Hz (which is a frequency higher than the spectral content of the pressure due to the mechanical ventilator) and the amplitude smaller than 2.5 cmH$_2$O peak-to-peak.

The procedure followed by the operator is as follows:
setting of the positive end-expiratory pressure (PEEP) equivalent or little higher than 0 cmH$_2$O;
insufflating step (progressive increase of the positive end-expiratory pressure) and sampling in some predetermined pressure values (samples from 100 to 106);
desufflating step (progressive decrease of the positive end-expiratory pressure) and sampling in some predetermined pressure values (samples from 107 to 112);
empirical verification of the derecruitment (FIG. 3) or non derecruitment (FIG. 2) situation;
identification of the optimal positive pressure, which is equivalent to the maximum value of the resulting inspiratory average reactance, which is the maximum of the desufflating curve (sample 110);
finally, the positive end-expiratory pressure is set to an optimal value.

Such a procedure takes a few minutes and only requires a partial alteration of the respiration of the patient 2.

A variant of the apparatus 1 may be made, according to which the electronic processor 12 also controls the ventilator 3 and sets the positive end-expiratory pressure thereof, and may therefore carry out the cycle of samplings in an automatic manner.

Furthermore, algorithms allowing to identify the presence of derecruitment on the basis of the analysis of the graph resulting from the samplings and recognise the maximum value (sample 110) of inspiratory average reactance may be implemented.

Well-known computing algorithms may also be used to obtain the maximum value of the respiratory reactance.

A computerised mechanical ventilator may also be made which, as well as imposing the respiratory flow, further allows to autonomously generate the additional pressure component, which in the suggested embodiment, is due to the speaker 15.

The invention also relates to a procedure for the detection of the optimal positive end-expiratory pressure in the course of respiration by means of a mechanical ventilator (3), which comprises the generation of a pressure component (P$^{stim}$) with a frequency harmonic higher than the spectral content of the respiratory pressure (P$^{resp}$), which may be due to a mechanical ventilator (3), and the following steps:
first step: setting of the positive end-expiratory pressure to a value near 0 cmH$_2$O;
second step: pressure (P) and flow (Flow) sampling and computing of the associated inspiratory average reactance ($X_{rs}$) for increasing values of positive end-expiratory pressure (PEEP);

third step: pressure (P) and flow (Flow) sampling and computing of the associated inspiratory average reactance ($X_{rs}$) for decreasing values of positive end-expiratory pressure (PEEP);

fourth step: verifying the derecruitment from the analysis of the resulting values of inspiratory average reactance ($X_{rs}$);

fifth step: identifying the optimal positive end-expiratory pressure (PEEP) (110);

sixth step: setting the optimal positive end-expiratory pressure (PEEP) by controlling the mechanical ventilator (3).

Such a procedure may also be integrated with a breath by breath monitoring step to detect derecruitment phenomena in the course of time and identify the best time for a new recruitment manoeuvre.

A procedure may also be used, allowing to detect the continuous distension pressure in the course of the high frequency oscillatory ventilation.

The same approach may be used in a totally similar manner to that described above to determine the optimal PEEP (in this application the CDP has the same role as the PEEP).

Figure 10:
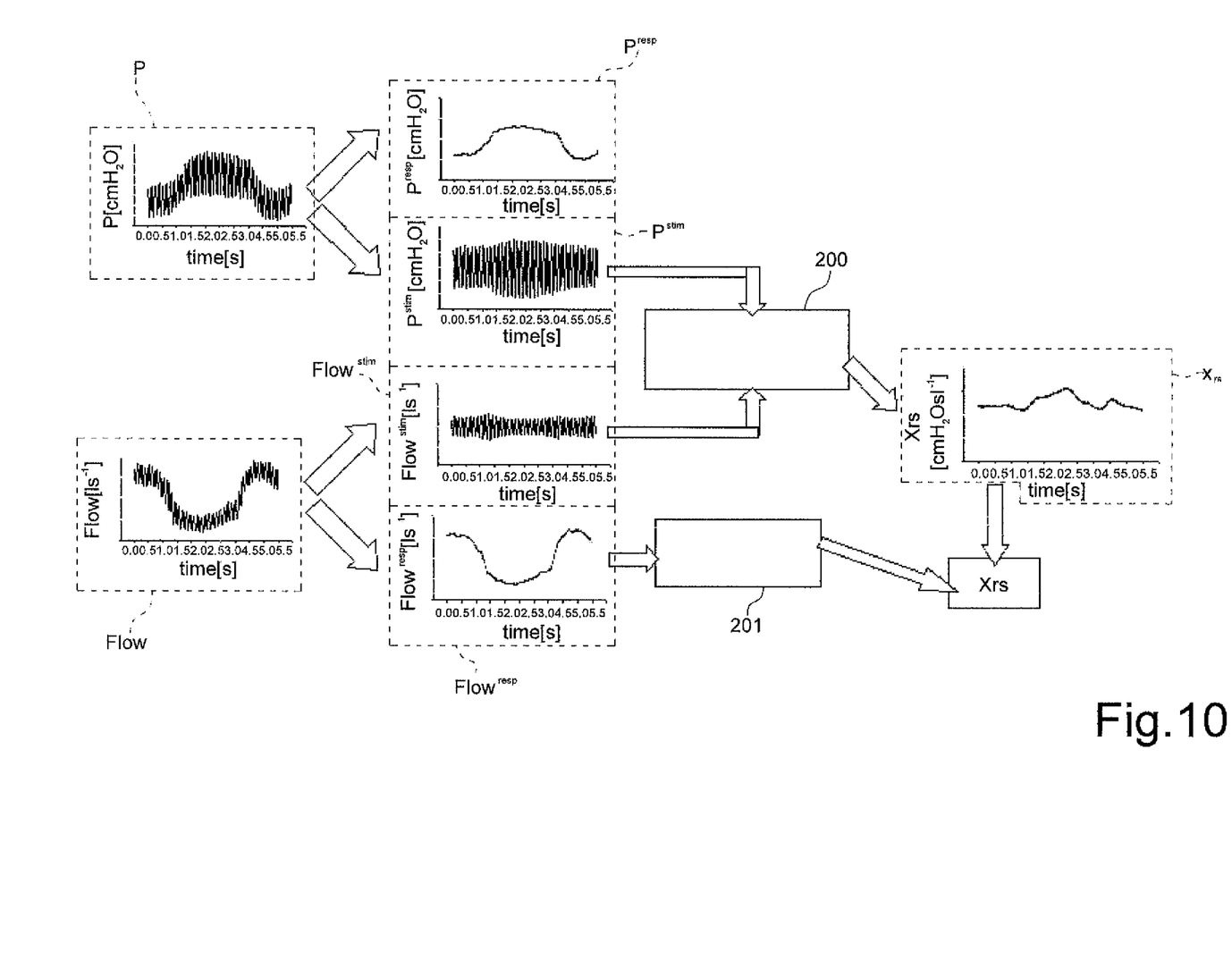
FIG. 10 shows a computing method for the inspiratory average reactance ($X_{rs}$)

An algorithm, shown in FIG. 10, is now described for the computation of the inspiratory average reactance $X_{rs}$ that may be implemented for instance in the electronic processor 12.

The pressure P to which the patient is subjected, measured by the use of the above said devices (transducer 10, analogue-digital convertor 11, electronic processor 12) is divided, by the use of known digital filters, so as to obtain the respiratory component $P^{resp}$ imposed by the mechanical ventilator 3 and the additional component $P^{stim}$.

Similarly, the air flow Flow, measured by the use of the above said devices (pneumotachograph 8, transducer 9, analogue-digital convertor 11, electronic processor 12) is divided in the low frequency component $Flow^{resp}$ and the high frequency component $Flow^{stim}$.

The periods of time during which an inspiration occurs may be obtained from the $Flow^{resp}$ analysis (state 201). These are the times in which $Flow^{resp}>0$.

Instead, the inspiratory point reactance $x_{rs}$ is obtained in state 200 according to methods disclosed by European patent EP1551293.

The computation of the inspiratory average reactance $X_{rs}$ is therefore simply obtained by means of the average of the inspiratory point reactance $x_{rs}$ during the inspiratory phase. Such an average may be obtained, for instance, in an inspiratory period, that is, with reference to FIGS. 4 and 9, in the time period between 0 and $t_1$.

Figure 11:
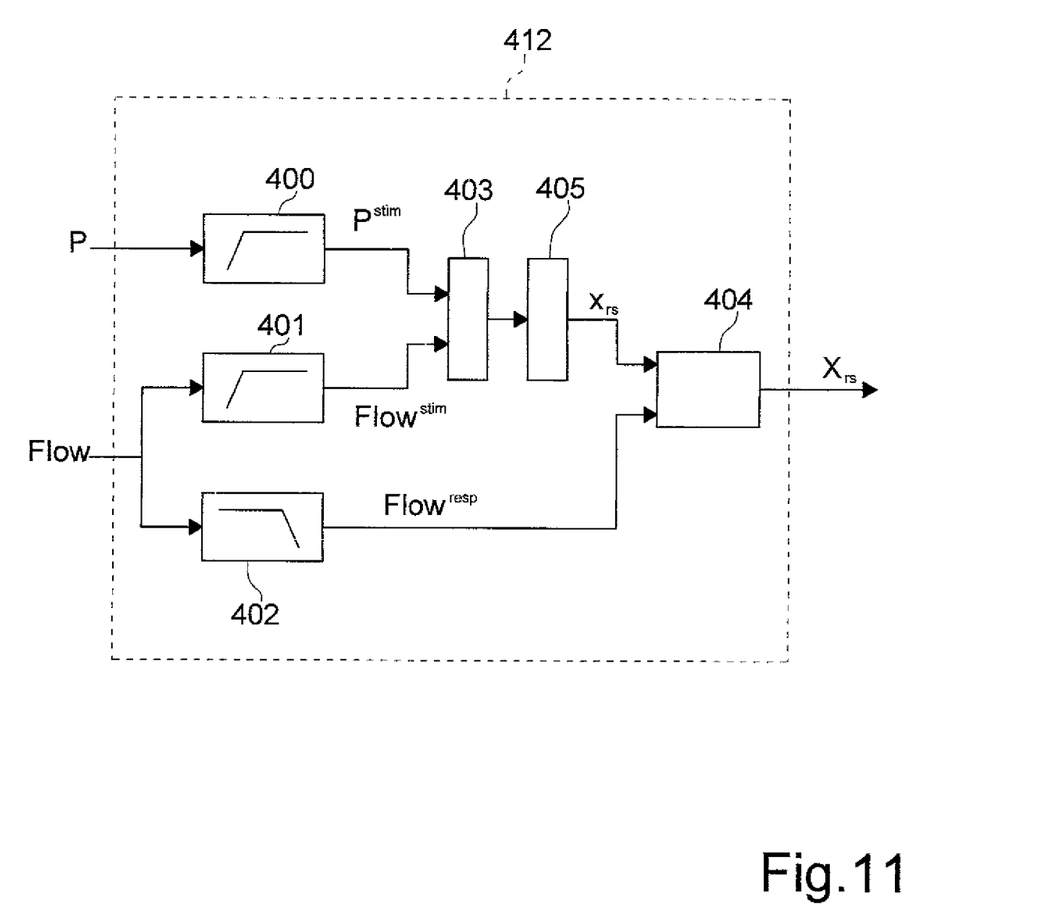
FIG. 11 shows a block diagram of a computing means allowing to compute the inspiratory average reactance ($X_{rs}$).

A possible block diagram of a computing means 412 allowing to compute the inspiratory average reactance $X_{rs}$ is now described and shown in FIG. 11.

The pressure P, to which the patient 2 is subjected, is filtered by means of a high pass filter 400 in order to obtain $P^{stim}$. The flow, Flow, is also filtered both by a high pass filter 401 in order to obtain $Flow^{stim}$ and by a low pass filter $Flow^{resp}$.

$P^{stim}$ and $Flow^{stim}$ are the input of block 403, which may provide the impedance of the respiratory system in output, on the basis of the voltage and current values respectively equivalent to $P^{stim}$ and $Flow^{stim}$, as described by European patent EP1551293. Block 405 allows to separate the imaginary part of such an impedance and provide the inspiratory point reactance $x_{rs}$ in output.

$Flow^{resp}$ and $x_{rs}$ are the inputs of block 404; such a block computes the average of $x_{rs}$ during inspiration (the duration of the inspiration is deduced from $Flow^{resp}$); the inspiratory average reactance $X_{rs}$ is given at the output of block 404.

The invention claimed is:

1. An apparatus for respiratory support and non-invasive detection of alveolar derecruitment for patients suffering from respiratory failure, said apparatus comprising:
   conduits for the passage of air from and to the airways of a patient,
   a mechanical ventilator for carrying out respiratory functions by supply of air under pressure to said conduits means to allow imposition of an additional pressure component (Pstim) of at least one prefixed frequency,
   and further comprising transducers of pressure to electric signals, transducers of flow to electric signals applied to said conduits and computing means for processing said electric signals resulting from both of said transducers of pressure and transducers of flow, the additional pressure imposed being based on the output of said computing means so as to obtain a value of the inspiratory reactance (Xrs), varying the value of the positive end-expiratory pressure (PEEP) indicative of the state of pulmonary derecruitment, and then
   said mechanical ventilator providing a settable PEEP corresponding to the maximum value of the respiratory reactance (Xrs).

2. An apparatus according to claim 1, wherein said apparatus includes means for generating a pressure component which has at least a frequency and amplitude harmonic suitable to obtain said inspiratory reactance (Xrs) is periodic with a period longer than the harmonic content of the respiratory frequency of said patient, said apparatus ventilating said patient by inspiration/expiration.

3. An apparatus according to claim 1, wherein said means for carrying out the respiratory functions comprise a high frequency oscillating ventilator allowing imposition of a periodic pressure having a frequency and an amplitude suitable to allow obtaining said inspiratory reactance.

4. An apparatus according to claim 3, wherein said high frequency ventilator provides a settable continuous distension pressure.

5. An apparatus according to claim 1 wherein said computing means automatically controls the settings of said means for carrying out respiratory functions, said computing means being provided with algorithms adapted to determine the maximum value of inspiratory reactance (Xrs).

6. An apparatus according to claim 1 which comprises a low pass filter obtained by means of a narrow and long tube.

7. An apparatus according to claim 1 wherein said computing means are connected, by means of an amplifier, to said speaker so as to control an inspiration/expiration pressure component ($P^{resp}$).

8. An apparatus according to claim 1 wherein said means to allow imposition of an additional pressure component is a speaker.

* * * * *